United States Patent [19]

Welt

[11] Patent Number: 4,502,476

[45] Date of Patent: Mar. 5, 1985

[54] PROTECTIVE EYE COVER

[76] Inventor: Claire Doolin Welt, 1137 Schilling Way, Mt. Shasta, Calif. 96067

[21] Appl. No.: 409,091

[22] Filed: Aug. 18, 1982

[51] Int. Cl.³ .............................................. A61F 13/00
[52] U.S. Cl. ................................ 128/132 R; 128/163; 2/15
[58] Field of Search ...................... 126/163, 132; 2/12, 2/15

[56] References Cited

U.S. PATENT DOCUMENTS

| 1,489,145 | 4/1924 | O'Keefe | 128/163 |
| 1,553,010 | 9/1925 | Terry et al. | |
| 1,917,117 | 7/1933 | Hines | 128/163 |
| 2,533,526 | 12/1950 | Snyder | 128/163 |
| 3,541,608 | 11/1970 | Otwell | 128/163 X |
| 3,780,379 | 12/1973 | Kampman | |
| 4,190,054 | 2/1980 | Brennan | |

FOREIGN PATENT DOCUMENTS

| 841,203 | 4/1952 | Fed. Rep. of Germany | 128/163 |
| 140863 | 6/1930 | Switzerland | 128/163 |

Primary Examiner—Stephen C. Pellegrino
Attorney, Agent, or Firm—Bernard, Rothwell & Brown

[57] ABSTRACT

A protective eye cover designed to cover and protect the eyes of infants undergoing treatment for hyperbilirubinemia (jaundice). The eye cover is comprised of an eye band with eye pads positioned to cover the infant's eyes, a scalp band which passes over the parietal region of the infant's head, and an occiput band which passes below the infant's occipital protuberance. The bands are each attached to a first and a second ear piece. The eye cover affords a soft, comfortable fit while remaining secure and in place on even the most active infant.

11 Claims, 3 Drawing Figures

PROTECTIVE EYE COVER

BACKGROUND OF THE INVENTION

1. Field of the Invention

The invention relates to a novel protective eye cover for infants. The eye cover is designed to cover and protect the eyes of infants undergoing treatment for hyperbilirubinemia (jaundice). This treatment consists of exposing an infant's entire body to blue fluorescent light for a period of several days. During this time, the infant's eyes must be covered and protected from the intense and constant light.

2. Prior Art

Previous attempts to provide protection for an infant's eyes while undergoing treatment for hyperbilirubinemia have involved placing cotton pads over the eyes and securing the pads with adhesive tape placed at the temples and the nose. This type of eye shield often caused skin irritation and pressure areas.

A prior art eye shield for infants is described in U.S. Pat. No. 3,541,608. This patent shows an eye shield for infants with a headband and a chin strap plus Velcro fastening means. The chin strap required to retain the eye shield in position on the infant's head may cause choking or impede breathing.

SUMMARY OF THE INVENTION

This invention provides a shield that will cover and protect the eyes of the most active infant from light without becoming dislodged which does not cause skin irritation or pressure areas. This invention provides an eye shield with an adjustable band that insures a secure and comfortable fit for each infant in a particular weight range, e.g., 2-4 lbs., 5-7 lbs., or 7-10 lbs.

This invention overcomes the disadvantages of the prior art devices by providing an eye cover that is maintained on an infant's head by an adjustable elastic band, rather than adhesive tape, and which passes below an infant's occipital protuberance, rather than under the chin for anchoring on the head. The eye cover of this invention is substantially comprised of three bands and two ear pieces. The bands are attached to each ear piece and it is the ear pieces that maintain each band at its proper angle to ensure a secure and comfortable fit on each infant's head. It is the triangular design effected by the ear pieces that is the main feature of this invention.

DESCRIPTION OF THE EMBODIMENT

Figure 1:
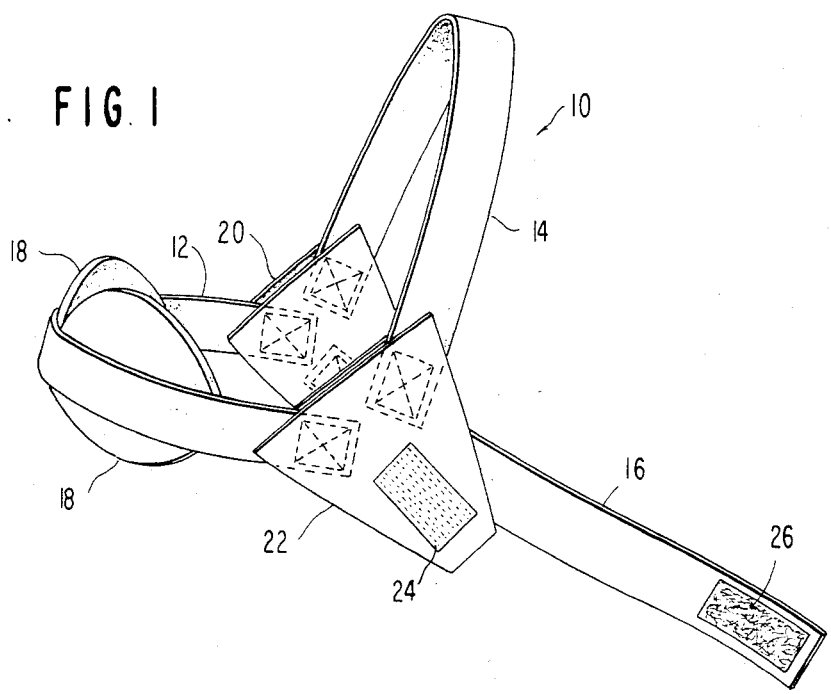
FIG. 1 is a perspective view of the eye shield of this invention prior to being applied to an infant's head.

Referring now to the drawing, a protective eye shield generally indicated at 10 is shown in FIG. 1. The eye shield 10 is comprised of an eye band 12, a scalp band 14, an adjustable occiput band 16, eye pads 18, right ear piece 20, left ear piece 22, Velcro hook section 24, and Velcro soft section 26. The protective eye pads 18 are positioned on the eye band 12 to cover the infant's eyes. The eye band 12 is attached to the right ear piece 20 and the left ear piece 22. The scalp band 14 is attached to the right ear piece 20 and the left ear piece 22. The adjustable occiput band 16 is attached to the right ear piece 20 and the left ear piece 22.

Figure 3:
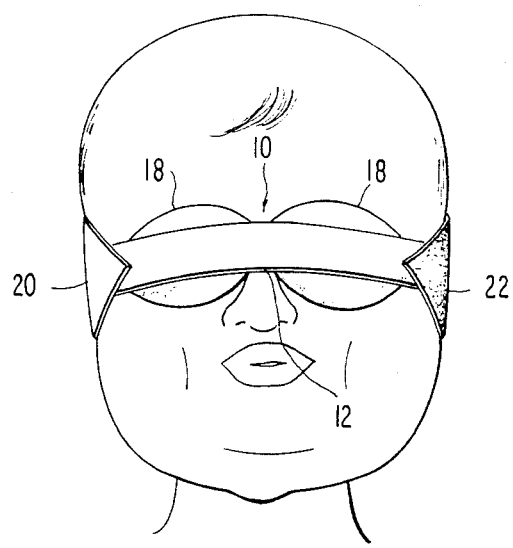
FIG. 3 is a front elevation view of the eye shield applied to an infant's head.

As shown in FIG. 3, the eye band 12 is attached to the right ear piece 20 and the left ear piece 22 so that the protective eye pads 18 will pass over the infant's eyes.

Figure 2:
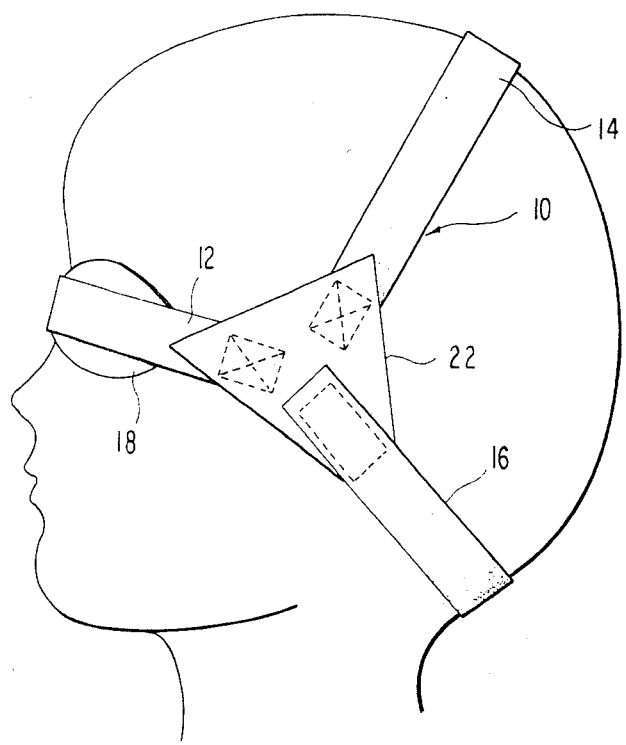
FIG. 2 is a side elevation view of the eye shield applied to an infant's head.

As shown in FIG. 2, the scalp band 14 is attached to the ear piece 22 so that the scalp band will pass over the parietal region of the infant's head. Also, as shown in FIG. 2, the adjustable occiput band 16 is attached to the left ear piece 22 so that the occiput band will pass below the infant's occipital protuberance. The occiput band 16 serves as the anchor strap of the eye shield, for if the infant pulls the band down towards its neck, this will only serve to pull the eye shield tighter around the eyes, and if the infant tries to pull the occiput band up, he will be prevented from doing so by his occipital protuberance. As shown in FIGS. 1 and 2, it is the ear pieces 20 and 22 that hold and maintain the eye strap 12, the scalp band 14, and the occiput band 16 at their proper angles.

In a preferred embodiment of this invention, the eye band is permanently attached to the right ear piece 20 and the left ear piece 22, the scalp band 14 is permanently attached to the right ear piece 20 and the left ear piece 22, and the occiput band is permanently attached to the right ear piece 20 and is adjustably attachable and detachable to the left ear piece 22. In the most preferred embodiment of this invention, the eye band 12 is sewn to the right ear piece 20 and the left ear piece 22, the scalp band 14 is sewn to the right ear piece 20 and the left ear piece 22, and the occiput band 16 is sewn to the right ear piece 20 and is adjustably attachable and detachable to the left ear piece 22. In these two embodiments an adjustably attachable and detachable hook and pile means (e.g., Velcro) is attached to the occiput band 16 and the left ear piece 22 to provide an adjustably attachable and detachable connection between the occiput band 16 and the left ear piece 22. The Velcro hook section 24 is attached to the left ear piece 22 and the Velcro soft section 26 is attached to the occiput band 16.

In the preferred embodiments of this invention, the right ear piece 20 and the left ear piece 22 are comprised of substantially triangular woven fabric. Also, the eye band 12, the scalp band 14, and the occiput band 16 are constructed of elastic material. Finally, the protective eye pads 18 are made of woven fabric with a cotton flannel liner wherein the cotton flannel liner has four layers of cotton flannel.

I claim:

1. A protective eye cover for infants comprising a chin-strapless eye cover assembly, the assembly including:
   (a) a first ear piece and a second ear piece;
   (b) an eye band with protective eye pads positioned thereon to cover the infant's eyes;
   (c) means attaching the eye band to the first ear piece and the second ear piece;
   (d) a scalp band;
   (e) means attaching the scalp band to the first ear piece and the second ear piece to pass said scalp band over the parietal region of the infant's head;
   (f) an occiput band;
   (g) means attaching the occiput band to the first ear piece and the second ear piece to pass said occiput band below the infant's occipital protuberance, the occiput band being adjustably attachable and detachable to the second ear piece.

2. The protective eye cover of claim 1 wherein the eye band is permanently attached to the first and the second ear piece, the scalp band is permanently attached to the first and the second ear piece, and the occiput band is permanently attached to the first ear piece.

3. The protective eye cover of claim 2 wherein the eye band is sewn to the first and the second ear piece, the scalp band is sewn to the first and second ear piece, and the occiput band is sewn to the first ear piece and is adjustably attachable and detachable to the second ear piece.

4. The protective eye cover of claim 2 or 3 wherein an adjustably attachable and detachable hook and pile means is attached to the occiput band and the second ear piece.

5. The protective eye cover of claim 1 or 2 wherein the first ear piece and the second ear piece are substantially triangular.

6. The protective eye cover of claim 5 wherein the first ear piece and the second ear piece are comprised of woven fabric.

7. The protective eye cover of claim 1 or 2 wherein the eye band, the scalp band, and the occiput band are constructed of elastic material.

8. The protective eye cover of claim 1 or 2 wherein the protective eye pads are comprised of woven fabric with a cotton flannel liner.

9. The protective eye cover of claim 6 wherein the cotton flannel liner is comprised of four layers of cotton flannel.

10. A protective eye cover for infants comprising a chin-strapless eye cover assembly, the assembly including:
   (a) a first substantially triangular fabric ear piece and a second substantially triangular fabric ear piece;
   (b) an elastic eye band with its ends permanently sewn to the first and the second ear piece and having protective fabric, cotton flannel lined, eye pads positioned thereon to cover the infant's eyes;
   (c) an elastic scalp band with its ends permanently sewn to the first and the second ear piece to pass said scalp band over the parietal region of the infant's head;
   (d) an elastic occiput band with one end permanently sewn to the first ear piece and the other end adjustably attachable and detachable with hook and pile means to the second ear pieces to pass said occiput band below the infant's occipital protuberance.

11. The protective eye cover of claim 10 wherein the hook and pile means comprises pile means attached to the occiput band and hook means attached to the second ear piece to provide an adjustably attachable and detachable connection between the occiput band and the second ear piece.

* * * * *